United States Patent [19]
Kozlow, Sr.

[11] 4,304,333
[45] Dec. 8, 1981

[54] ADHESIVE BANDAGE AND PACKAGE

[76] Inventor: William Kozlow, Sr., 419 Forest Dr., Union, N.J. 07083

[21] Appl. No.: 84,886

[22] Filed: Oct. 15, 1979

[51] Int. Cl.³ .............................................. A61B 17/06
[52] U.S. Cl. .................................... 206/441; 206/484
[58] Field of Search ............................... 206/441, 484

[56] References Cited

U.S. PATENT DOCUMENTS

| | | | |
|---|---|---|---|
| 2,969,144 | 1/1961 | Zackheim | 206/441 |
| 2,969,145 | 1/1961 | Hannauer, Jr. | 206/441 |
| 3,313,405 | 4/1967 | Blackford | 206/441 |
| 4,182,449 | 1/1980 | Kozlow | 206/441 |

*Primary Examiner*—Joseph Man-Fu Moy
*Attorney, Agent, or Firm*—Martha G. Pugh

[57] ABSTRACT

An adhesive bandage and package is provided wherein the package portion of the bandage serves as means by which the bandage may be applied to the wound without affecting sterility. More precisely, the adhesive bandage, having a backing, and a pad with a facing, is folded with the uncoated face of the backing back to back and is covered by a suitable covering material that is heat, pressure, or ultrasonic sealed on the four sides parallel to the edges of the cover. One end portion of the cover extends beyond the seal and serves as means for opening the package. The other end portion also extends beyond the seal and serves as means to apply the bandage.

9 Claims, 4 Drawing Figures

ADHESIVE BANDAGE AND PACKAGE

BACKGROUND OF THE INVENTION

The adhesive bandages of prior art are packaged in packages which are separate from the bandages. The package serves primarily to maintain sterility of the bandage. Upon removal of the bandage from the package one is to hold onto the extended portions of a release coated paper or plastic material covering the face and the adhesive portions of the bandage in order to apply the same to the wound.

My invention obviates the use of the separate packaging thus providing an economic advantage. It also eliminates the unnecessary separate handling of the adhesive bandage thereby minimizing the chance of contamination and the adhesive bandage is easier and faster to apply because the package is used as the means to apply the adhesive bandage.

PURPOSE OF THE INVENTION

The purpose of my invention is to provide an adhesive bandage and package in which the conventionally used separate package is eliminated, to improve handling, to insure sterility, and to simplify means to apply the adhesive bandage to a wound. Another purpose of my invention is to reduce the amount of material used in an adhesive bandage and package and thus obtain an economic gain.

SUMMARY OF THE INVENTION

The purposes and objectives of the present invention are accomplished in an adhesive bandage and package wherein the adhesive bandage is composed of a backing of a suitable material on one side of which and about centrally positioned is a pad and the remaining area of the same side of the backing is coated with a pressure sensitive adhesive; said bandage is folded on a transverse axis in such manner that the two sections of the uncoated face of the backing face each other and the coated two sections and pad are facing outward. There is placed over the bandage a plastic or a release coated paper or foil, completely covering the adhesive portions and pad portion of the bandage and overlapping all edges with a greater portion extending outward on both ends. Said cover material is then heat, pressure or ultrasonic sealed beyond the periphery of the bandage and parallel to the cover edges. The portion of the cover beyond the seal that is adjacent to the bandage ends serves as the means to open the package, and the portion of cover beyond the seal adjacent to fold serves as means to apply the bandage. The purpose and objectives accomplished will be more readily understood from the detailed description that follows.

DETAILED DESCRIPTION OF THE DRAWINGS

Figure 1:
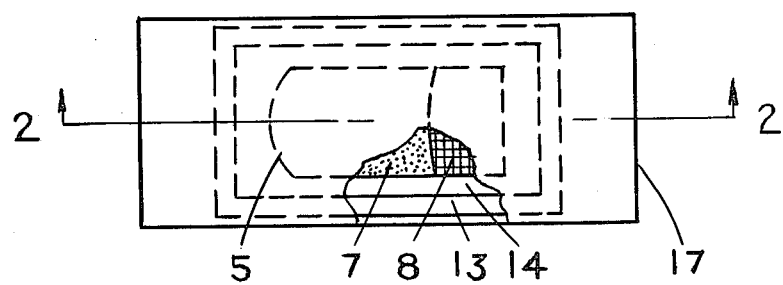
FIG. 1 is a plan view of the adhesive bandage and package. The adhesive bandage is folded across its width exactly in half with the backing back to back and the adhesive coating and the bandage pad facing out. The bandage is covered with two pieces of a covering material of substantially the same shape as the bandage but its dimensions are larger so that it extends somewhat beyond the edges of the folded bandage. The package is sealed on four sides parallel to the four edges of the folded adhesive bandage. There is a space between the inside edge of the package seal and the four edges of the adhesive bandage. The seal is formed by heat and pressure, pressure or ultrasonics. The package is longer on both ends beyond the package seal thus forming the package peel tabs and the peel tabs have a straight shape.
Figure 2:
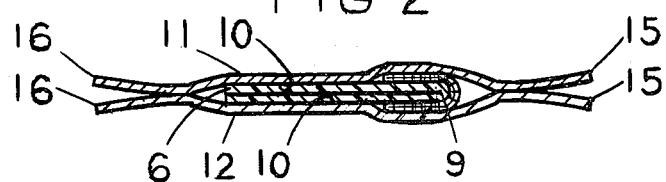
FIG. 2 is a cross section of the adhesive bandage and package shown in FIG. 1 taken along line 2.

Referring to FIGS. 1,2,3 and 4 the adhesive bandage 5 has a perforated plastic backing 6, that is entirely coated on one face with a pressure sensitive adhesive 7. The bottom face of an absorbant pad 8 is stuck onto the adhesive 7 in the center of the adhesive face. The absorbant pad 8 has a wound release facing.

The adhesive bandage 5 is folded with the adhesive 7 and the absorbant pad 8 facing out and the uncoated face of the backing 6 is back to back. The fold 9 is across the bandage width at its center as in FIGS. 1 and 2 or the fold 9 could be at one edge of the bandage pad as in FIGS. 3 and 4.

Figure 3:
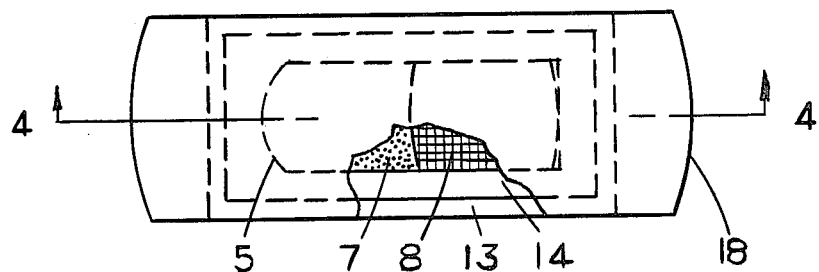
FIG. 3 is a plan view of another embodiment of the present invention of the adhesive bandage and package. The materials and construction are the same as FIG. 1 except the adhesive bandage is folded across its width with the fold at one edge of bandage pad, and the package peel tabs have a curved shape.
Figure 4:
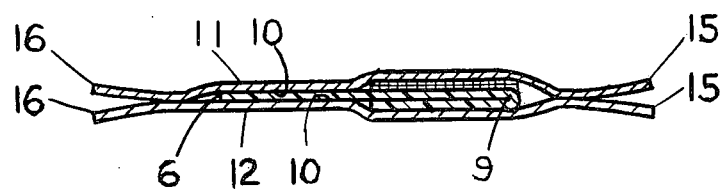
FIG. 4 is a cross section of the adhesive bandage and package shown in FIG. 3 taken along line 4.

The package in FIGS. 1 and 3 is made from two pieces of plastic or from paper, foil or similiar material that is coated on one face with plastic or silicone. The coated face 10 on package side 11 is placed on the adhesive face 7 on one side of the folded adhesive bandage 5. The coated face 10 of package side 12 is placed on the adhesive face 7 on the opposite side of the folded adhesive bandage.

The two pieces of the package 11 and 12 are sealed together by heat and pressure, pressure or ultrasonics. The package seal 13 is parallel to the four edges of the package and the four edges of the folded adhesive bandage 5. There is a space 14 between the inner edge of the package seal 13 and the four edges of the folded adhesive bandage 5.

Package sides 11 and 12 extend on both ends of the package beyond the outside edge of the package seal 13 to form the package peel tabs. The package peel tabs 15 are on the end of the package nearest the fold 9 on the adhesive bandage 5, and the package peel tabs 16 are on the end of the package nearest the two ends of the adhesive bandage 5. The peel tabs have a straight shape 17 or a curved shape 18.

The adhesive bandage and package FIGS. 1 thru 4 for sterilization by steam or gas has a paper package and there is no coating on both inside faces of the package in the area covering the space 14 between the edges of the adhesive bandage 5 and the inner edge of the package seal 13.

The package seal 13 in FIGS. 1 thru 4 is formed by heat and pressure or ultrasonics on plastic packages or packages that are coated on the inside in the seal area 13 with plastic.

The package seal 13 in FIGS. 1 thru 4 is formed by pressure on all packages coated on the inside in the seal area 13 with a pressure sensitive adhesive.

DESCRIPTION OF MATERIALS OF CONSTRUCTION

The adhesive bandage is made from materials customarily used to make an adhesive bandage. More specifically the adhesive bandage of the present invention can be made of materials as follows: In a conventionally used bandage there are three essential components: a backing, adhesive, and a pad for contacting the wound. The backing is made from a soft plastic and is perforated throughout. The adhesive is a pressure sensitive material composed of a rubber or plastic compound, and the bandage pad is made from plastic foam, paper, cotton or gauze with or without a nonadherant plastic material on the top face for wound release.

The package or covering utilizes materials customarily used in making adhesive bandages and their wrappers. The package is made from paper or foil, with a plastic or silicone coating on one side or from plastic. A package with a coating of a pressure sensitive adhesive compound of rubber or plastic in the seal area is closed by pressure and a package with a plastic coating in the seal area is closed by heat and pressure or ultrasonics.

What is claimed is:

1. An adhesive bandage and package comprising in combination:
    a folded adhesive bandage having a backing strip having one surface coated with a pressure sensitive coating, and the other surface substantially uncoated, and a pad centrally positioned on the coated side of said backing strip intermediate the opposite ends thereof, said adhesive bandage being folded transversely so that at least one end of said backing strip is back-to-back against the uncoated side;
    covering means for said folded adhesive bandage constructed to serve as a package and for applying said bandage, said covering means comprising a pair of layers of flexible material disposed so that opposite said layers are adjacent to the coated sides on opposite ends of said adhesive bandage, said layers each having a shape substantially similar to said folded adhesive bandage but disposed to extend somewhat beyond the edges of said folded adhesive bandage; said layers being sealed together along lines parallel to and outside of the edges of said folded adhesive bandage, said covering layers extending away from the seals at opposite ends of said covering means, thereby forming a set of peel tabs on each end of the package, whereby one set of said peel tabs adjacent to at least one end of said backing strip serves for opening said package, and whereby the other set of said peel tabs adjacent to the transverse fold of said bandage serves for applying said bandage with minimum contamination.

2. An adhesive bandage and package in accordance with claim 1 wherein said adhesive bandage is folded along a transverse axis thereof at equidistance from the ends.

3. An adhesive bandage and package in accordance with claim 1 wherein said adhesive bandage is folded transversely along a line at located at unequal distances from the opposite ends.

4. The adhesive bandage and package in accordance with claim 1 wherein said covering means comprises a material selected from the group consisting of plastic, paper, and foil.

5. The adhesive bandage and package in accordance with claim 1 wherein said covering means comprises two pieces of material, each piece being of a different material.

6. The adhesive bandage and package in accordance with claim 1 wherein said seal is formed by heat and pressure, pressure or ultrasonics.

7. An adhesive bandage and package comprising in combination:
    an adhesive bandage having a backing strip including a pressure sensitive coating on one face, the other face being substantially uncoated, and a pad centrally positioned on said coated face of said backing strip, said adhesive bandage being folded on its transverse axis so that portions of said uncoated face upon folding are back-to-back;
    a pair of paper covering layers for said folded adhesive bandage, said paper covering layers disposed adjacent opposite faces of said folded adhesive bandage and of substantially the same shape as said folded adhesive bandage, said layers being sealed parallel to and slightly beyond the edges of said folded bandage, the ends of said covering layers extending away from the seals on opposite ends of said package, forming a set of peel tabs at each of said ends, whereby one set of said peel tabs adjacent to at least one end of said backing strip serves for opening said package, and whereby the other set of said peel tabs adjacent to the transverse fold of said bandage serves for applying said bandage with minimum contamination.

8. The adhesive bandage and package in accordance with claim 7 wherein said paper covering layers are coated with a plastic material on the inside portion facing the bandage which is contained therein.

9. The adhesive bandage and package in accordance with claim 7 wherein said paper covering layers on the portions thereof facing the adhesive bandage are plastic coated only where they contact the bandage and in the seal areas of said covering layers.

* * * * *